(12) United States Patent
Grunenberg et al.

(10) Patent No.: US 8,466,280 B2
(45) Date of Patent: Jun. 18, 2013

(54) CO-CRYSTAL COMPOUND OF RIVAROXABAN AND MALONIC ACID

(75) Inventors: Alfons Grunenberg, Dormagen (DE); Karsten Fähnrich, Grenzach-Whylen (DE); Olaf Queckenberg, Bergisch-Gladbach (DE); Christiane Reute, Leverkusen (DE); Birgit Keil, Düsseldorf (DE); Karen Sue Gushurst, West Lafayette, IN (US); Ezra John Still, West Lafayette, IN (US)

(73) Assignee: Bayer Intellectual Property GmbH, Monheim am Rhein (DE)

( * ) Notice: Subject to any disclaimer, the term of this patent is extended or adjusted under 35 U.S.C. 154(b) by 192 days.

(21) Appl. No.: 12/997,474

(22) PCT Filed: Jun. 3, 2009

(86) PCT No.: PCT/EP2009/003952
§ 371 (c)(1),
(2), (4) Date: Feb. 24, 2011

(87) PCT Pub. No.: WO2009/149851
PCT Pub. Date: Dec. 17, 2009

(65) Prior Publication Data
US 2011/0152266 A1    Jun. 23, 2011

(30) Foreign Application Priority Data
Jun. 12, 2008 (DE) .......................... 10 2008 028 071

(51) Int. Cl.
*C07D 265/30* (2006.01)
*A61K 31/5377* (2006.01)

(52) U.S. Cl.
USPC .......................................... 544/106; 514/376

(58) Field of Classification Search
None
See application file for complete search history.

(56) References Cited

U.S. PATENT DOCUMENTS

| 2003/0153610 | A1* | 8/2003 | Straub et al. ................... 514/376 |
| 2005/0182055 | A1 | 8/2005 | Berwe et al. |
| 2010/0137274 | A1 | 6/2010 | Straub et al. |
| 2010/0152189 | A1 | 6/2010 | Grunenberg et al. |

FOREIGN PATENT DOCUMENTS

| WO | WO-0147919 | 7/2001 |
| WO | WO-2005/068456 | 7/2005 |
| WO | WO-2007/039132 | 4/2007 |

OTHER PUBLICATIONS

International Search Report for international application No. PCT/EP2009/003952.

* cited by examiner

*Primary Examiner* — Jason M Nolan
*Assistant Examiner* — Ana Z Muresan
(74) *Attorney, Agent, or Firm* — Buchanan Ingersoll & Rooney

(57) ABSTRACT

The present invention relates to a novel cocrystal compound of 5-chloro-N-({(5S)-2-oxo-3-[4-(3-oxo-4-morpholinyl)phenyl]-1,3-oxazolidin-5-yl}methyl)-2-thiophenecarboxamide (rivaroxaban) and malonic acid, to processes for its preparation, to medicaments comprising this compound and to their use for controlling diseases.

11 Claims, 7 Drawing Sheets

Figure 1: DSC (continuous line) and TGA (dashed line) thermograms
A) Rivaroxaban/malonic acid cocrystal
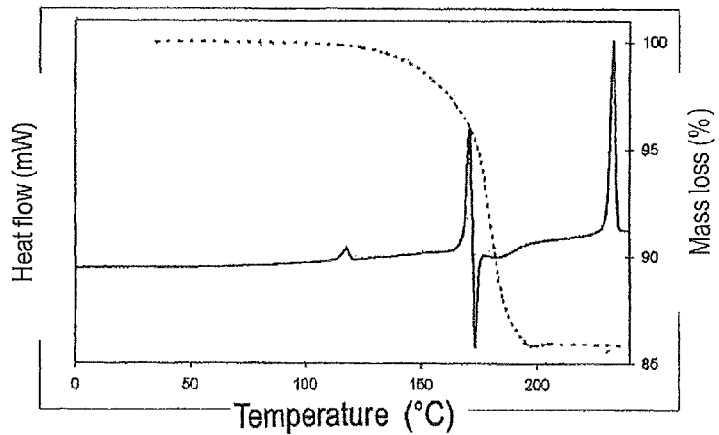
B) Rivaroxaban modification I
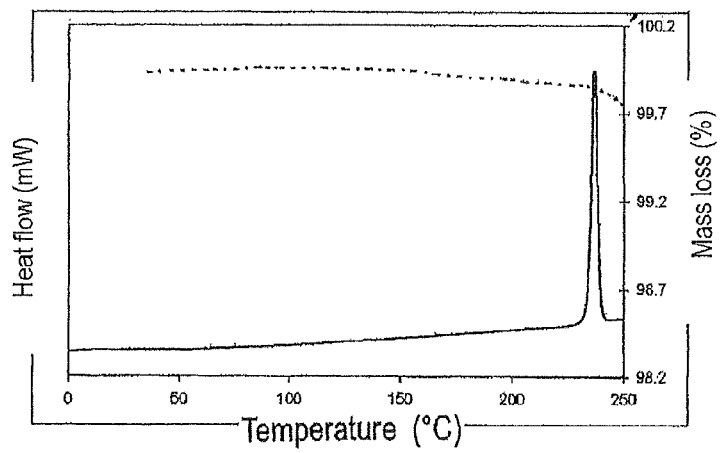
C) Malonic acid
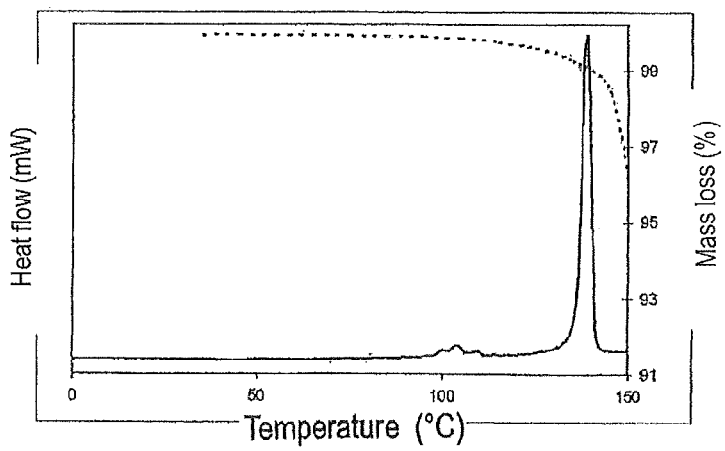

Figure 2: X-ray diffractograms of rivaroxaban/malonic acid cocrystal, rivaroxaban modification I, and malonic acid (from top to bottom)
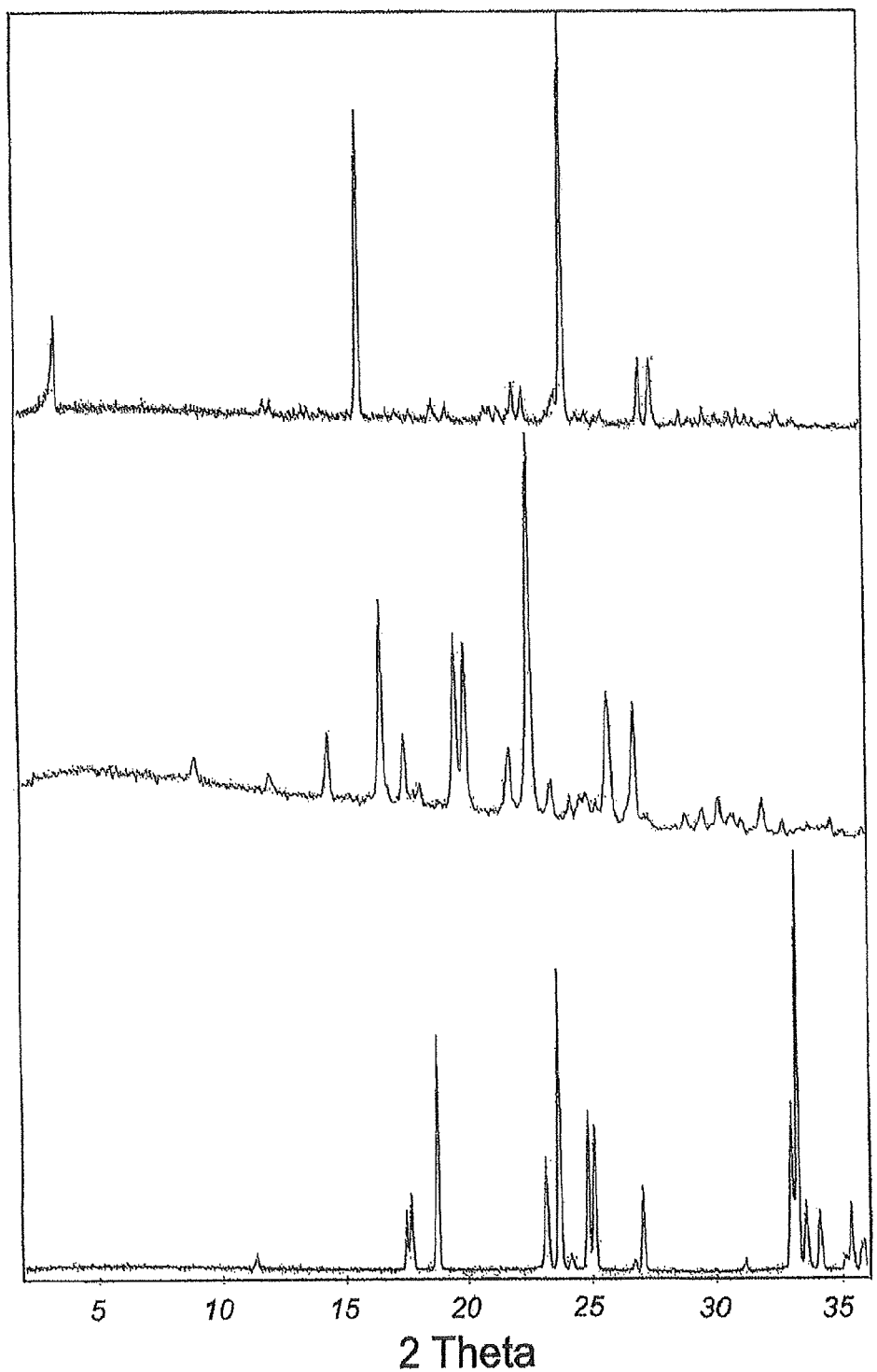

Figure 3: IR spectra of rivaroxaban/malonic acid cocrystal, rivaroxaban modification I, and malonic acid (from top to bottom)
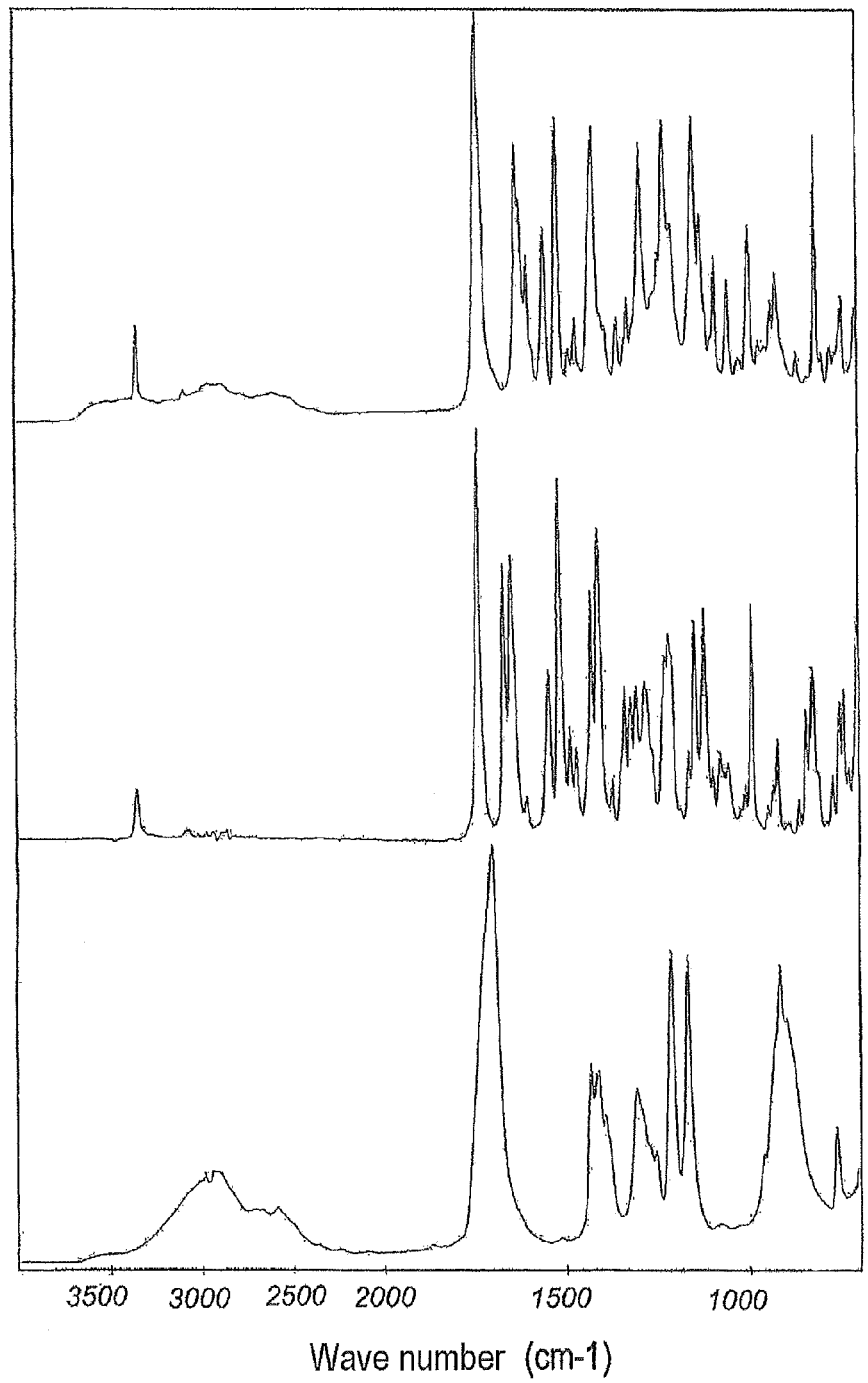

Figure 4: Raman spectra of rivaroxaban/malonic acid cocrystal, rivaroxaban modification I, and malonic acid (from top to bottom)
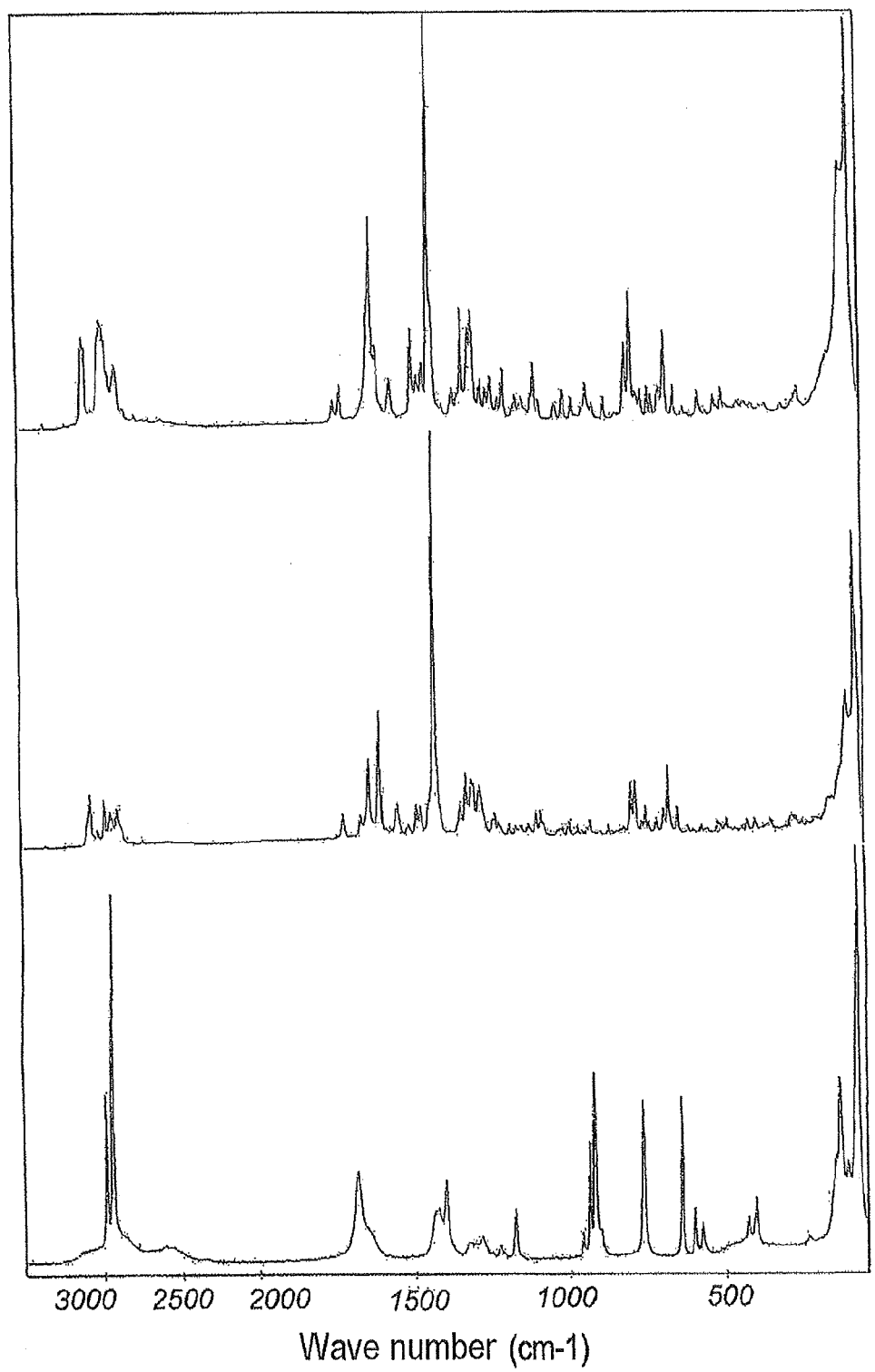

Figure 5: FIR spectra of rivaroxaban/malonic acid cocrystal, rivaroxaban modification I, and malonic acid (from top to bottom)
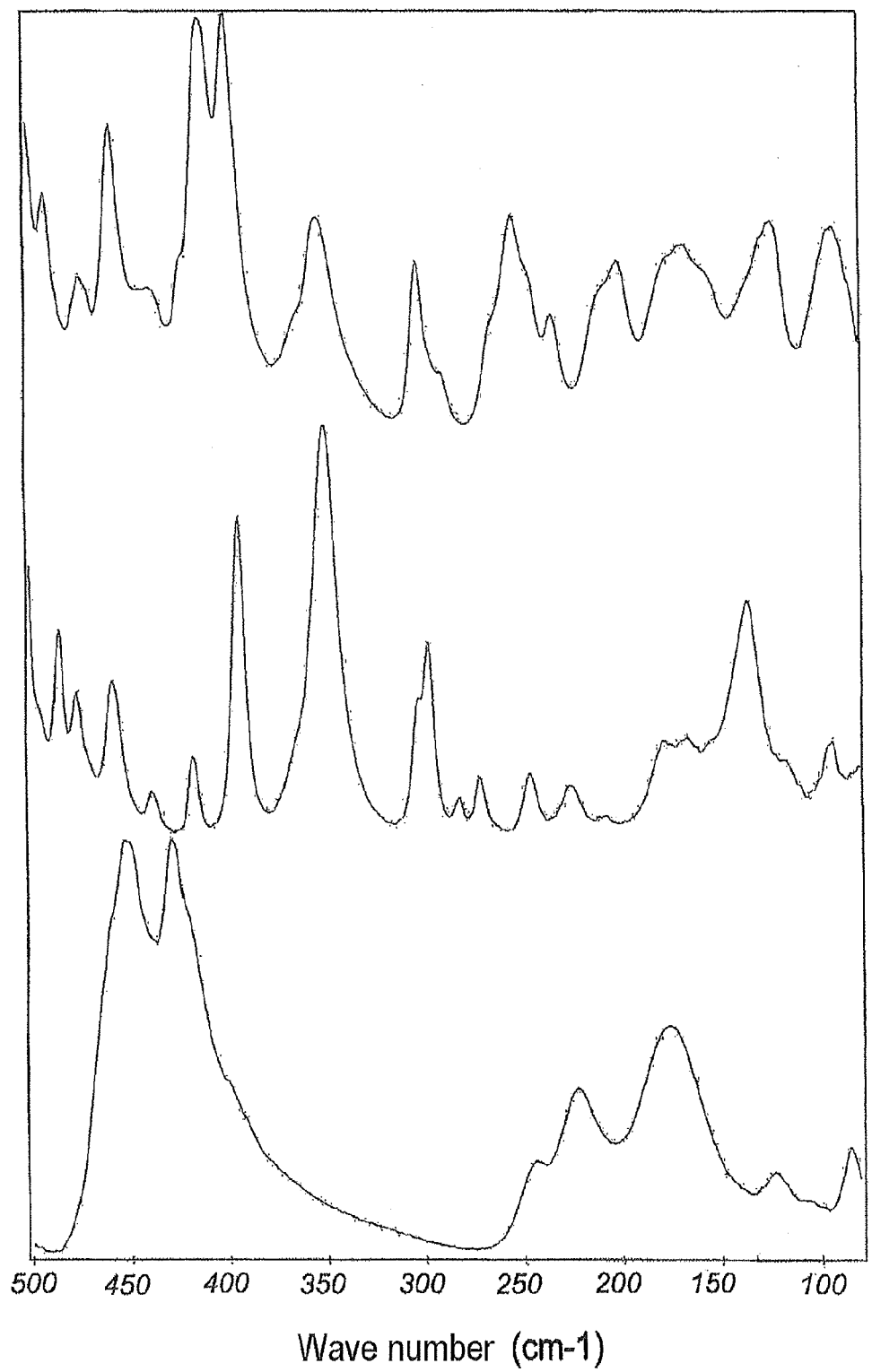

Figure 6: NIR spectra of rivaroxaban/malonic acid cocrystal, rivaroxaban modification I, and malonic acid (from top to bottom)
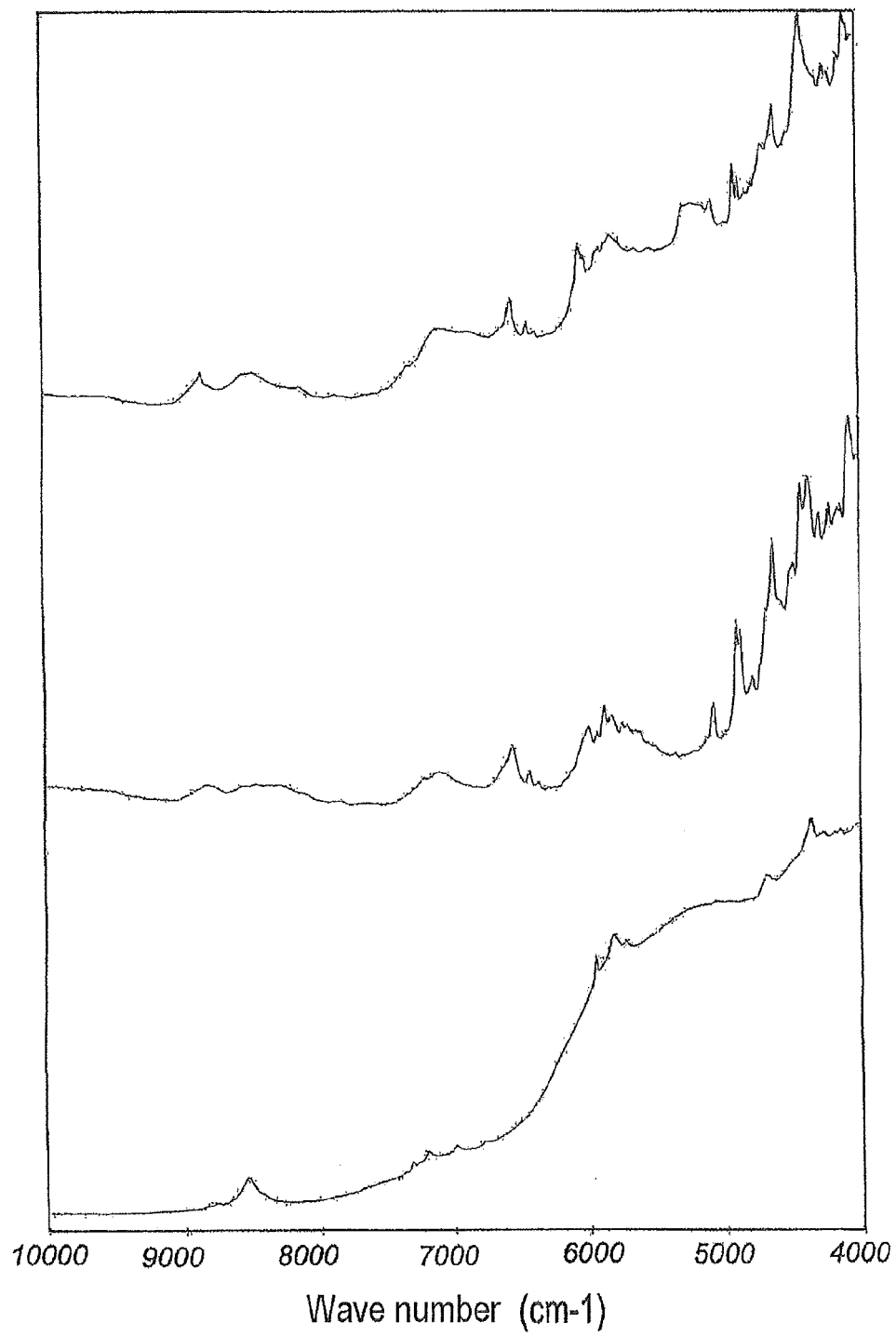

Figure 7: ¹³C-MAS NMR spectra of rivaroxaban/malonic acid cocrystal, rivaroxaban modification I, and malonic acid (from top to bottom)
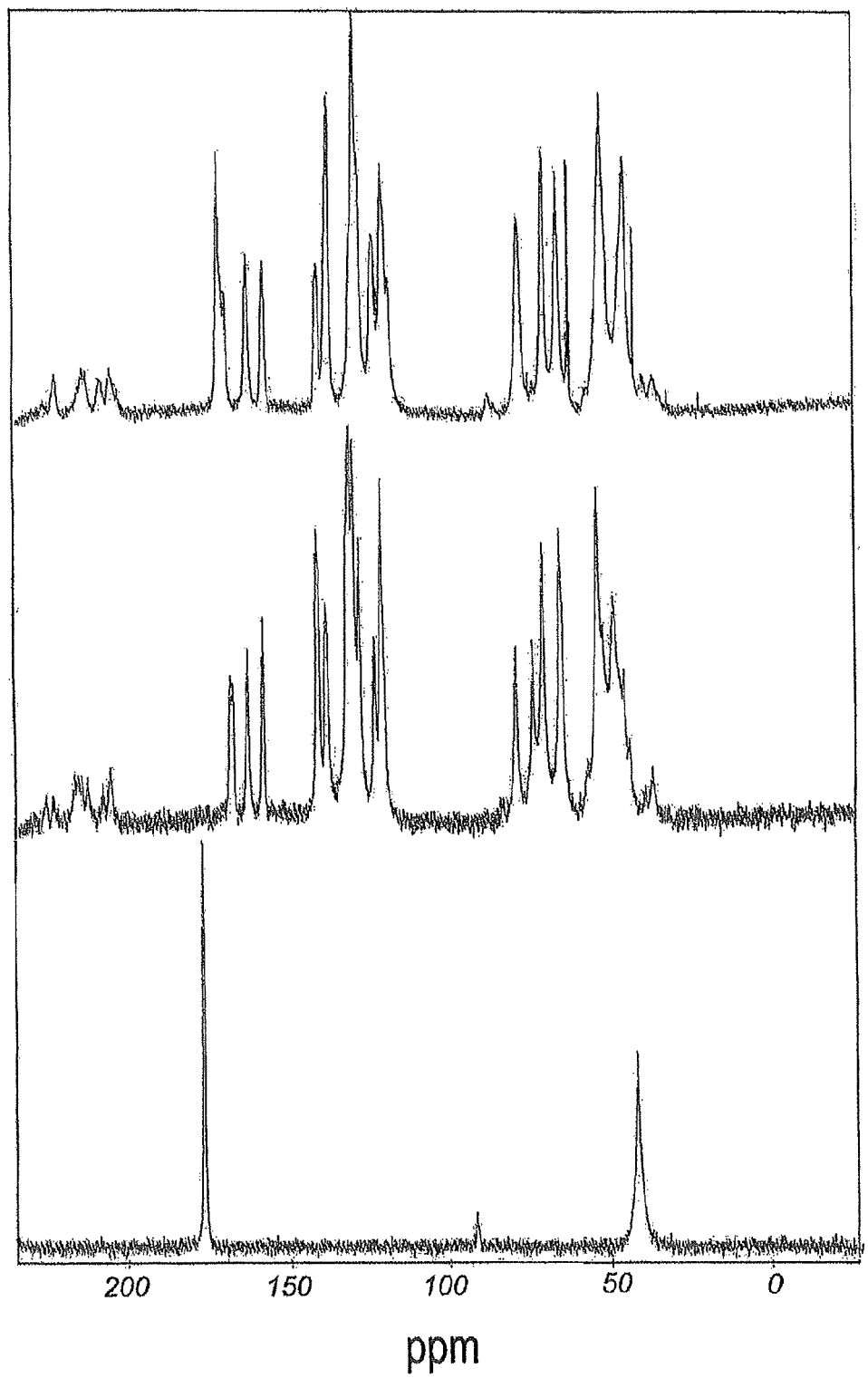

CO-CRYSTAL COMPOUND OF RIVAROXABAN AND MALONIC ACID

RELATED APPLICATIONS

This application is a national stage application (under 35 U.S.C. §371) of PCT/EP2009/003952, filed Jun. 3, 2009, which claims benefit of German application 102008028071.2, filed Jun. 12, 2008.

The present invention relates to a novel cocrystal compound of 5-chloro-N-({(5S)-2-oxo-3-[4-(3-oxo-4-morpholinyl)phenyl]-1,3-oxazolidin-5-yl}methyl)-2-thiophenecarboxamide (rivaroxaban) and malonic acid, to processes for its preparation, to medicaments comprising this compound and to their use for controlling diseases.

The compound 5-chloro-N-({(5S)-2-oxo-3-[4-(3-oxo-4-morpholinyl)phenyl]-1,3-oxazolidin-5-yl}methyl)-2-thiophenecarboxamide (rivaroxaban) is known from WO 01/47919 and corresponds to the formula (I):

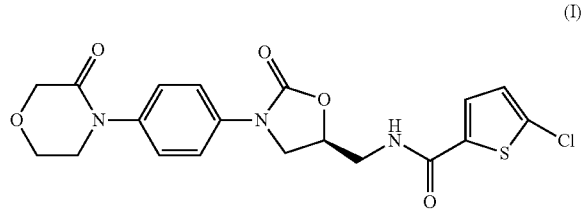 [SMILES: O=C(NC[C@H]1CN(c2ccc(N3CCOCC3=O)cc2)C(=O)O1)c1ccc(Cl)s1]

(I)

The compound of the formula (I) is a low-molecular-weight oral inhibitor of the blood coagulation factor Xa which can be used for the prophylaxis, secondary prophylaxis and/or treatment of various thromboembolic disorders (see WO 01/47919, the disclosure of which is hereby incorporated by reference), in particular of myocardial infarction, angina pectoris (including unstable angina), reocclusions and restenoses after angioplasty or aortocoronary bypass, cerebral stroke, transitory ischemic attacks, peripheral arterial occlusive diseases, pulmonary embolisms or deep venous thromboses.

The compound of the formula (I) can be prepared as described in WO 01/47919. Here, the compound of the formula (I) is obtained in a crystal modification referred to hereinbelow as modification I. Modification I has a melting point of 230° C. and a characteristic X-ray diffractogram, IR spectrum, Raman spectrum, FIR spectrum, NIR spectrum and $^{13}$C solid NMR spectrum (Tables 1-7, FIGS. 1-7).

The present invention provides the compound rivaroxaban/malonic acid cocrystal of the formula (II)

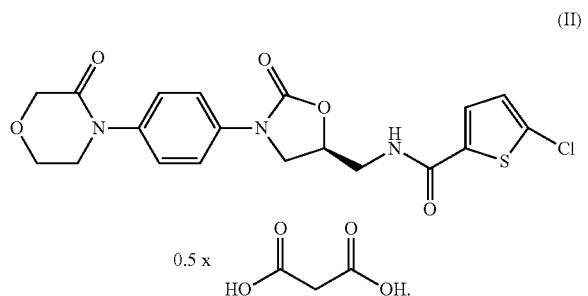

(II)

Surprisingly, rivaroxaban/malonic acid cocrystal of the formula (II) has a solubility which is higher by a factor of 2.5 than that of the compound of the formula (I) in modification I.

By the use according to the invention of the compound as rivaroxaban/malonic acid cocrystal of the formula (II), it is ensured that, compared to the known compound of the formula (I) in modification I, a solubility which is 2.5 times higher is achieved.

FIG. 1: DSC (continuous line) and TGA (dashed line) thermograms
  A) rivaroxaban/malonic acid cocrystal
  B) rivaroxaban modification I
  C) malonic acid FIG. 2: X-ray diffractograms of rivaroxaban/malonic acid cocrystal, rivaroxaban modification I, and malonic acid (from top to bottom)

FIG. 3: IR spectra of rivaroxaban/malonic acid cocrystal, rivaroxaban modification I, and malonic acid (from top to bottom)

FIG. 4: Raman spectra of rivaroxaban/malonic acid cocrystal, rivaroxaban modification I, and malonic acid (from top to bottom)

FIG. 5: FIR spectra of rivaroxaban/malonic acid cocrystal, rivaroxaban modification I, and malonic acid (from top to bottom)

FIG. 6: NIR spectra of rivaroxaban/malonic acid cocrystal, rivaroxaban modification I, and malonic acid (from top to bottom)

FIG. 7: $^{13}$C-MAS NMR spectra of rivaroxaban/malonic acid cocrystal, rivaroxaban modification I, and malonic acid (from top to bottom)

Cocrystal: A cocrystal is a mixed crystal which consists of two different components (A. I. Kitaigorodskii, Mixed crystals, Springer-Verlag, New York, 1984) which are solid at room temperature (C. B Aakeröy, D. J. Salmon, Building cocrystals with molecular sense and supramolecular sensibility, Cryst. Eng. Comm. 7 (2005) 439-448).

Compared to the compound of the formula (I) in modification I and malonic acid of the formula (III), rivaroxaban/malonic acid cocrystal of the formula (II) has a clearly distinguishable X-ray diffractogram, IR spectrum, NIR spectrum, FIR spectrum, Raman spectrum and $^{13}$C solid NMR spectrum (FIGS. 2-7). The compound of the formula (II) melts at 160° C. and is transformed at about 115° C. and is thus clearly distinguishable from the compound of the formula (I) in modification I (melting point 230° C.) and malonic acid of the formula (III) (melting point about 135° C. and transition point about 85-110° C.). In contrast to the compound of the formula (I) in modification I, the compound of the formula (II) has a mass loss of 14%.

Malonic acid, compound of the formula (III)

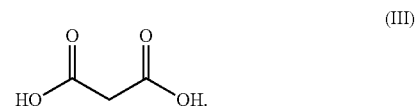

(III)

Single-crystal structural analysis confirms that rivaroxaban/malonic acid cocrystal is present in a molar ratio of 2:1 (Table 8).

The present invention furthermore provides the compound rivaroxaban/malonic acid cocrystal of the formula (II) which has a reflex at a 2-theta angle of 15.8 in the X-ray diffractogram.

The present invention furthermore provides the compound rivaroxaban/malonic acid cocrystal of the formula (II) which has a peak at 1617 cm$^{-1}$ in the Raman spectrum.

In pharmaceutical formulations, the compound of the formula (II) according to the invention is used in high purity. For reasons of stability, a pharmaceutical formulation comprises mainly the compound of the formula (II) and no major proportions of any other form such as, for example, another modification or a solvate of the compound of the formula (II). Preferably, the medicament comprises more than 90% by weight, particularly preferably more than 95% by weight, of the compound of the formula (II), based on the total amount of the compound of the formula (II) present.

The invention furthermore provides the use of the compound of the formula (II) for the treatment and/or prophylaxis of disorders, preferably thromboembolic disorders and/or thromboembolic complications.

The "thromboembolic disorders" within the meaning of the present invention in particular include disorders such as myocardial infarction with ST segment elevation (STEM) and without ST segment elevation (non-STEMI), stable angina pectoris, unstable angina pectoris, reocclusions and restenoses after coronary inventions such as angioplasty or aortocoronary bypass, peripheral arterial occlusive diseases, pulmonary embolisms, deep venous thromboses and renal vein thromboses, transitory ischemic attacks, and thrombotic and thromboembolic cerebral stroke.

The compound according to the invention is therefore also suitable for the prevention and treatment of cardiogenic thromboembolisms, such as, for example, cerebral ischemias, stroke and systemic thromboembolisms and ischemias in patients with acute, intermittent or persistent cardiac arrhythmias, such as, for example, atrial fibrillation, and those who undergo cardioversion, furthermore in the case of patients with heart valve diseases or with artificial heart valves. In addition, the compound according to the invention is suitable for the treatment of disseminated intravasal clotting (DIC).

Thromboembolic complications furthermore occur in microangiopathic haemolytic anaemias, extracorporal blood circulations, such as haemodialysis, and heart valve prostheses.

Moreover, the compound according to the invention is also suitable for the prophylaxis and/or treatment of atherosclerotic vascular diseases and inflammatory diseases such as rheumatic diseases of the locomotor system, and in addition also for the prophylaxis and/or treatment of Alzheimer's disease. Moreover, the compound according to the invention can be employed for the inhibition of tumour growth and metastasis formation, in microangiopathies, age-related macula degeneration, diabetic retinopathy, diabetic nephropathy and other microvascular diseases, and for the prevention and treatment of thromboembolic complications, such as, for example, venous thromboembolisms, in tumour patients, in particular those undergo major surgical interventions or chemo- or radiotherapy.

The compound according to the invention can additionally also be employed for the prevention of coagulation ex vivo, for example for the preservation of blood and plasma products, for the cleaning/pretreatment of catheters and other medical aids and equipment, for the coating of artificial surfaces of medical aids and equipment employed in vivo or ex vivo or in biological samples which contain factor Xa.

The present invention furthermore provides the use of the compound according to the invention for the treatment and/or prophylaxis of diseases, in particular of the aforementioned diseases.

The present invention furthermore provides the use of the compound according to the invention for preparing a medicament for the treatment and/or prophylaxis of diseases, in particular of the aforementioned diseases.

The present invention furthermore provides a method for the treatment and/or prophylaxis of diseases, in particular of the aforementioned diseases, using an anticoagulatory amount of the compound according to the invention.

The present invention furthermore provides a method for preventing the coagulation of blood in vitro, in particular in preserved blood or biological samples comprising factor Xa, which is characterized in that an anticoagulatory amount of the compound according to the invention is added.

The present invention furthermore provides medicaments comprising the compound according to the invention and one or more further active compounds, in particular for the treatment and/or prophylaxis of the aforementioned diseases. Suitable combination active compounds which may be mentioned by way of example and preferably are:

Lipid-lowering agents, in particular HMG-CoA-(3-hydroxy-3-methylglutaryl-coenzyme A)-reductase inhibitors;

coronary therapeutics/vasodilators, in particular ACE (angiotensin converting enzyme) inhibitors; AII (angiotensin II) receptor antagonists; β-adrenoceptor antagonists; alpha-1-adrenoceptor-antagonists; diuretics; calcium channel blockers; substances which bring about an increase in cyclic guanosine monophosphate (cGMP), such as, for example, stimulators of soluble guanylate cyclase;

plasminogen activators (thrombolytics/fibrinolytics) and thrombolysis/fibrinolysis-increasing compounds such as inhibitors of the plasminogen activator inhibitor (PAI inhibitors) or inhibitors of the thrombin-activated fibrinolysis inhibitor (TAFI inhibitors);

substances having anticoagulatory activity (anticoagulants);

substances inhibiting platelet aggregation (platelet aggregation inhibitors, thrombocyte aggregation inhibitors);

and fibrinogen receptor antagonists (glycoprotein IIb/IIIa antagonists).

The present invention furthermore provides medicaments comprising the compound according to the invention, usually together with one or more inert nontoxic pharmaceutically suitable auxiliaries, and their use for the purposes mentioned above.

The compound according to the invention can act systemically and/or locally. For this purpose, it can be administered in a suitable manner, such as, for example, orally, parenterally, pulmonarily, nasally, sublingually, lingually, buccally, rectally, dermally, transdermally, conjunctivally, otically or as an implant or stent.

For these administration routes, the compound according to the invention can be administered in suitable administration forms.

For oral administration, administration forms functioning according to the prior art, releasing the compound according to the invention rapidly and/or in modified form, which contain the compound of the formula (II), such as, for example, tablets (uncoated or coated tablets, for example with enteric coatings or coatings which dissolve with a delay or are insoluble, which control the release of the compound according to the invention), tablets disintegrating rapidly in the oral cavity and/or films/wafers, films/lyophilisates, capsules (for example hard or soft gelatin capsules), coated tablets, granules, pellets, powders, suspensions or aerosols are suitable.

Parenteral administration can take place with circumvention of an absorption step (for example intravenously, intraarterially, intracardially, intraspinally or intralumbarly) or with intervention of an absorption (for example intramuscularly, subcutaneously, intracutaneously, percutaneously or intraperitoneally). For parenteral administration, suitable administration forms are, inter alia, injection and infusion preparations in the form of suspensions, lyophilisates or sterile powders.

For the other administration routes, for example, inhalation pharmaceutical forms (inter alia powder inhalers, nebulizers), tablets to be administered lingually, sublingually or buccally, films/wafers or capsules, suppositories, ear or eye preparations, vaginal capsules, aqueous suspensions (lotions, shake mixtures), lipophilic suspensions, ointments, creams, transdermal therapeutic systems (for example patches), milk, pastes, foams, dusting powders, implants or stents are suitable.

Preference is given to oral or parenteral administration, in particular to oral administration.

The compound according to the invention can be converted to the administration forms mentioned. This can take place in a manner known per se by mixing with inert, nontoxic, pharmaceutically suitable auxiliaries. These auxiliaries include, inter alia, vehicles (for example microcrystalline cellulose, lactose, mannitol), solvents (for example liquid polyethylene glycols), emulsifiers and dispersants or wetting agents (for example sodium dodecylsulphate, polyoxysorbitan oleate), binders (for example polyvinylpyrrolidone), synthetic and natural polymers (for example albumin), stabilizers (for example antioxidants such as, for example, ascorbic acid), colorants (for example inorganic pigments such as, for example, iron oxides) and taste and/or odour corrigents.

In general it has proven advantageous in the case of parenteral administration to administer amounts of approximately 0.001 to 1 mg/kg of body weight, preferably approximately 0.01 to 0.5 mg/kg of body weight, to achieve effective results. In the case of oral administration, the dose is approximately 0.01 to 100 mg/kg of body weight, preferably approximately 0.01 to 20 mg/kg of body weight and very particularly preferably 0.1 to 10 mg/kg of body weight.

In spite of this, it may optionally be necessary to depart from the amounts mentioned, namely depending on body weight, route of administration, individual response to the active compound, type of preparation and time or interval at which administration takes place. Thus, in some cases, it may be sufficient to administer less than the minimum amount mentioned above, whereas in other cases the upper limit mentioned has to be exceeded. If relatively large amounts are administered, it may be advisable to divide these into a plurality of individual administrations over the course of the day.

The present invention furthermore provides a process for preparing the compound rivaroxaban/malonic acid cocrystal of the formula (II) by dissolving the active compound rivaroxaban of the formula (I) in modification I and the reagent malonic acid of the formula (III) in an inert solvent at a temperature between 50° C. and 90° C. and evaporating the solvent.

The present invention furthermore provides a process for preparing the compound rivaroxaban/malonic acid cocrystal of the formula (II) by dissolving the active compound rivaroxaban of the formula (I) in modification I and the reagent malonic acid of the formula (III) in an inert solvent in a molar ratio of 1:1 at a temperature between 50° C. and 90° C. The solvent is preferably evaporated between 20° C. and 25° C. This gives the compound rivaroxaban/malonic acid cocrystal of the formula (II).

The present invention furthermore provides a process for preparing the compound rivaroxaban/malonic acid cocrystal of the formula (II) by dissolving the active compound rivaroxaban of the formula (I) in modification I in an inert solvent with stirring and heating, preferably between 50° C. and 90° C., and adding 1.5 eq of malonic acid of the formula (III) to the hot solution. The volume of the solution is, preferably between 50° C. and 90° C., reduced to approximately half, the solution is transferred into another vessel and the vessel is closed. The solution is cooled at a temperature between 20° C. and 25° C. for 4 h. The crystals formed are isolated and dried. This gives the compound rivaroxaban/malonic acid cocrystal of the formula (II).

The present invention furthermore provides a process for preparing the compound rivaroxaban/malonic acid cocrystal of the formula (II) by dissolving the active compound rivaroxaban of the formula (I) in modification I and the reagent malonic acid of the formula (III) in an inert solvent in a molar ratio of 1:1 at a temperature between 50° C. and 90° C. The volume is reduced to approximately half, preferably between 50° C. and 90° C. The hot solution is seeded with crystals of the compound rivaroxaban/malonic acid cocrystal of the formula (II). The hot solution is cooled for a period of approximately 15 minutes, preferably to between 20° C. and 25° C. The precipitate is isolated and dried. This gives the compound rivaroxaban/malonic acid cocrystal of the formula (II).

The present invention furthermore provides a process for preparing the compound rivaroxaban/malonic acid cocrystal of the formula (II) by preparing a saturated solution of the reagent malonic acid of the formula (III) in an inert solvent, in which solution, preferably between 50° C. and 90° C., the active compound rivaroxaban of the formula (I) of modification I is dissolved. The solution is cooled slowly, preferably to 20° C.-25° C. After approximately 2 h, the precipitate is filtered off with suction and dried. This gives the compound rivaroxaban/malonic acid cocrystal of the formula (II).

The present invention furthermore provides a process for preparing the compound rivaroxaban/malonic acid cocrystal of the formula (II) by suspending the active compound rivaroxaban of the formula (I) in modification I and the reagent malonic acid of the formula (III) in an inert solvent at a temperature between 20° C. and 25° C. and isolating the precipitate.

The present invention furthermore provides a process for preparing the compound rivaroxaban/malonic acid cocrystal of the formula (II) by preparing a solution of the reagent malonic acid of the formula (III) in an inert solvent, in which solution, preferably between 20° C. and 25° C., the active compound rivaroxaban of the formula (I) in modification I is suspended. The suspension is stirred in a closed vessel for at least 48 h, preferably between 20° C. and 25° C. The precipitate is isolated and dried. This gives the compound rivaroxaban/malonic acid cocrystal of the formula (II).

Suitable inert solvents are lower alcohols, such as, for example, ethanol, 2-propanol or 2,2,2-trifluoroethanol, or ketones, such as, for example, acetone, or other solvents, such as, for example, acetonitrile. Preference is given to 2,2,2-trifluoroethanol or acetone.

The compound rivaroxaban/malonic acid cocrystal of the formula (II) is preferably prepared by dissolving malonic acid of the formula (III) and the active compound rivaroxaban of the formula (I) in modification I in a molar ratio of 1:1 in 2,2,2-trifluoroethanol, preferably between 50° C. and 90° C. The volume of the solution is reduced to approximately half. The precipitate obtained by seeding the hot solution with crystals of rivaroxaban/malonic acid cocrystal of the formula (II) is isolated and dried. This gives the compound rivaroxaban/malonic acid cocrystal of the formula (II).

The percentages in the tests and examples below are, unless indicated otherwise, percent by weight; parts are parts by weight. Solvent ratios, dilution ratios and stated concentrations of liquid/liquid solutions are in each case based on volume.

EXEMPLARY EMBODIMENTS

The thermograms were obtained using a diamond DSC or Pyris-1 differential scanning calorimeter and a Pyris-1 thermogravimetric analyzer from Perkin-Elmer. The X-ray diffractograms were recorded in a Stoe transmission diffractometer. The $^{13}$C MAS NMR spectra were recorded with a DMX 300 nuclear magnetic resonance spectrometer from Bruker. The IR, FIR, NIR and Raman spectra were recorded using the Fourier spectrometers Tensor 27/Miracle ATR (IR), IFS 66v (FIR), Vector 22/N (NIR) and RFS 100 (Raman) from Bruker.

Example 1

Rivaroxaban of the Formula (I) in Modification I

The preparation of modification I of the title compound is described in WO 01/47919.

Example 2

Preparation of Rivaroxaban/Malonic Acid Cocrystal

Example 2.1

27 mg of rivaroxaban of the formula (I) in modification I were dissolved in 3 ml of 2,2,2-trifluoroethanol and the solution was filtered through a 0.2 μm syringe filter. 0.2 ml of malonic acid solution [75 mg of malonic acid in 2 ml of methanol] was added to the solution. The solution was evaporated at room temperature and the crystals formed were dried. The crystals were examined by Raman spectroscopy and correspond to the title compound in formula (II).

Example 2.2

87 mg of rivaroxaban of the formula (I) in modification I were dissolved in 0.45 ml of 2,2,2-trifluoroethanol with stirring and heating between 70° C. and 80° C. 30 mg of malonic acid of the formula (III) were added to the hot solution. The volume of the solution was reduced to approximately 0.2 ml by heating the open vessel, and the hot solution was then transferred into another glass vessel. The vessel was closed and cooled at room temperature. After 4 h, the precipitate formed was filtered off with suction. The crystals were air-dried between 20° C. and 25° C. The crystals were examined by Raman spectroscopy and correspond to the title compound in formula (II).

Example 2.3

87 mg of rivaroxaban of the formula (I) in modification 1 and 21 mg of malonic acid of the formula (III) were dissolved in 0.5 ml of 2,2,2-trifluoroethanol with stirring and heating between 70° C. and 80° C. The volume of the solution was reduced to approximately 0.15 ml by heating the open vessel, and the hot solution was seeded with crystals of rivaroxaban/ malonic acid cocrystal of the formula (II). Over a period of 15-20 minutes, the solution was cooled to room temperature. The precipitate formed was filtered off with suction and air-dried between 20° C. and 25° C. The precipitate was examined by Raman spectroscopy and corresponds to the title compound of formula (II).

Example 2.4

871 mg of rivaroxaban of the formula (I) in modification I and 208 mg of malonic acid of the formula (III) were suspended in 5 ml of 2,2,2-trifluoroethanol and heated to 70° C. to 80° C. and dissolved. By heating between 70° C. and 80° C., the solution was evaporated to about 2.5 ml. The hot solution was seeded with crystals of rivaroxaban/malonic acid cocrystal of the formula (II) and cooled to room temperature over a period of 20 minutes. The precipitate formed was filtered off with suction and air-dried between 20° C. and 25° C. The precipitate was examined by Raman spectroscopy and corresponds to the title compound in formula (II).

Example 2.5

17 g of rivaroxaban of the formula (I) in modification 1 and 4 g of malonic acid of the formula (III) were suspended in 100 ml of 2,2,2-trifluoroethanol and heated to 50° C. to 90° C. and dissolved. The solution was evaporated to approximately 50 ml by heating between 50° C. and 90° C. The hot solution was seeded with crystals of rivaroxaban/malonic acid cocrystal of the formula (II) and cooled to room temperature over a period of 20 minutes. The precipitate formed was filtered off with suction and air-dried between 20° C. and 25° C. The precipitate was examined by Raman spectroscopy and corresponds to the title compound of the formula (II).

Example 2.6

800 mg of malonic acid of the formula (III) were dissolved in 3 ml of acetone and the solution was allowed to stand overnight. 33 mg of rivaroxaban of the formula (I) in modification I were added to 2 ml of this solution and suspended therein. The suspension was stirred at room temperature in a closed vessel for 48 h. The crystals were filtered off with suction and air-dried between 20° C. and 25° C. The crystals were examined by Raman spectroscopy and correspond to the title compound in formula (II).

Example 2.7

A saturated solution of malonic acid of the formula (III) in acetone was prepared. The solution was stirred between 20° C. and 25° C. for 12 h and the undissolved residue was filtered off using pleated filters. 3 ml of the saturated malonic acid solution were added to 103 mg of rivaroxaban of the formula (I) in modification I, and the rivaroxaban was dissolved in the solution between 50° C. and 90° C. under reflux. Over a period of 2 h, the solution was cooled to room temperature. The precipitate formed was filtered off with suction and air-dried between 20° C. and 25° C. The crystals were examined by Raman spectroscopy and correspond to the title compound in formula (II).

Example 2.8

A saturated solution of malonic acid of the formula (III) in ethanol was prepared. The solution was stirred between 20° C. and 25° C. for 12 h and the undissolved residue was filtered off using pleated filters. 3 ml of the saturated malonic acid solution were added to 103 mg of rivaroxaban of the formula (I) in modification I, and the rivaroxaban was dissolved in the solution between 50° C. and 90° C. under reflux. Over a period of 2 h, the solution was cooled to room temperature. The precipitate formed was filtered off with suction and air-dried between 20° C. and 25° C. The precipitate was examined by Raman spectroscopy and corresponds to the title compound in formula (II).

Example 2.9

A saturated solution of malonic acid of the formula (III) in 2-propanol was prepared. The solution was stirred between 20° C. and 25° C. for 12 h, and the undissolved residue was filtered off using pleated filters. 3 ml of the saturated malonic acid solution were added to 103 mg of rivaroxaban of the formula (I) in modification I, and the rivaroxaban was dissolved in the solution between 50° C. and 90° C. under reflux. Over a period of 2 h, the solution was cooled to room temperature. The precipitate formed was filtered off with suction and air-dried between 20° C. and 25° C. The precipitate was examined by Raman spectroscopy and corresponds to the title compound in formula (II).

Example 2.10

A suspension of malonic acid of the formula (III) in acetonitrile [1.7 g in 6 ml] was prepared. The suspension was stirred between 20° C. and 25° C. for 12 h. 4 ml of the malonic acid suspension were added to 103 mg of rivaroxaban of the formula (I) in modification I, and the mixture was stirred at room temperature for 4.5 days. The crystals were filtered off with suction and air-dried between 20° C. and 25° C. The crystals were examined by Raman spectroscopy and correspond to the title compound in formula (II).

TABLE 1

Differential scanning calorimetry and thermogravimetry

| | Rivaroxaban/ malonic acid cocrystal | Rivaroxaban modification I | Malonic acid |
|---|---|---|---|
| Melting point [° C.] | 230 | 230 | 135 |
| Transition point [° C.] | 170 | — | 85-110 |
| Mass loss [% by wt.] | 14 | 0.1 | <0.5 |

TABLE 2

X-ray diffractometry
Peak maxima

| Rivaroxaban/ malonic acid cocrystal [2 theta] | Rivaroxaban modification I [2 theta] | Malonic acid [2 theta] |
|---|---|---|
| 3.5 | 9.0 | 11.3 |
| 11.9 | 12.0 | 17.4 |
| 13.4 | 14.3 | 17.7 |
| 15.8 | 16.5 | 18.7 |
| 18.7 | 17.4 | 23.1 |
| 19.3 | 19.5 | 23.6 |
| 21.1 | 19.9 | 24.1 |
| 21.4 | 21.7 | 24.8 |
| 22.0 | 22.5 | 25.1 |
| 22.4 | 23.4 | 26.6 |
| 24.0 | 24.1 | 27.0 |
| 27.0 | 24.7 | 31.2 |
| 27.5 | 25.6 | 33.0 |
| 28.7 | 26.6 | 33.3 |
| 29.6 | 28.7 | 33.6 |

TABLE 2-continued

X-ray diffractometry
Peak maxima

| Rivaroxaban/ malonic acid cocrystal [2 theta] | Rivaroxaban modification I [2 theta] | Malonic acid [2 theta] |
|---|---|---|
| 31.0 | 29.4 | 34.1 |
| 32.6 | 30.1 | 35.3 |
| 36.2 | 31.8 | 35.9 |
| | 32.7 | 36.7 |
| | 34.5 | 37.4 |

TABLE 3

IR spectroscopy
Peak maxima

| Rivaroxaban/ malonic acid cocrystal [$cm^{-1}$] | Rivaroxaban modification I [$cm^{-1}$] | Malonic acid [$cm^{-1}$] |
|---|---|---|
| 3345 | 3354 | 2990 |
| 3092 | 3074 | 2946 |
| 2887 | 2977 | 2597 |
| 2604 | 2869 | 1701 |
| 1736 | 1736 | 1435 |
| 1629 | 1668 | 1416 |
| 1619 | 1646 | 1397 |
| 1601 | 1606 | 1311 |
| 1553 | 1546 | 1258 |
| 1518 | 1517 | 1216 |
| 1487 | 1486 | 1169 |
| 1469 | 1470 | 1082 |
| 1418 | 1429 | 961 |
| 1400 | 1411 | 919 |
| 1389 | 1374 | 901 |
| 1357 | 1340 | 770 |
| 1329 | 1324 | |
| 1292 | 1308 | |
| 1243 | 1285 | |
| 1228 | 1230 | |
| 1208 | 1219 | |
| 1145 | 1164 | |
| 1125 | 1147 | |
| 1089 | 1120 | |
| 1053 | 1099 | |
| 1025 | 1078 | |
| 995 | 1056 | |
| 967 | 1011 | |
| 933 | 992 | |
| 921 | 947 | |
| 866 | 932 | |
| 816 | 920 | |
| 798 | 891 | |
| 777 | 865 | |
| 746 | 846 | |
| 709 | 829 | |
| | 776 | |
| | 757 | |
| | 745 | |
| | 731 | |
| | 708 | |

TABLE 4

Raman spectroscopy
Peak maxima

| Rivaroxaban/malonic acid cocrystal [cm$^{-1}$] | Rivaroxaban modification I [cm$^{-1}$] | Malonic acid [cm$^{-1}$] |
| --- | --- | --- |
| 3347 | 3074 | 2990 |
| 3091 | 3024 | 2951 |
| 3077 | 2983 | 2611 |
| 2974 | 2944 | 1686 |
| 2889 | 2899 | 1428 |
| 2834 | 2736 | 1402 |
| 2760 | 2566 | 1284 |
| 2719 | 1722 | 1230 |
| 2593 | 1664 | 1179 |
| 1740 | 1638 | 960 |
| 1720 | 1605 | 938 |
| 1626 | 1548 | 921 |
| 1617 | 1512 | 765 |
| 1602 | 1485 | 641 |
| 1557 | 1473 | 601 |
| 1489 | 1445 | 579 |
| 1469 | 1428 | 432 |
| 1451 | 1343 | 407 |
| 1431 | 1325 | 244 |
| 1390 | 1316 | 145 |
| 1354 | 1307 | 121 |
| 1326 | 1300 | 85 |
| 1303 | 1280 | |
| 1292 | 1239 | |
| 1263 | 1232 | |
| 1246 | 1219 | |
| 1231 | 1185 | |
| 1209 | 1164 | |
| 1192 | 1148 | |
| 1152 | 1123 | |
| 1130 | 1098 | |
| 1101 | 1083 | |
| 1093 | 1011 | |
| 1076 | 990 | |
| 1026 | 963 | |
| 998 | 948 | |
| 970 | 922 | |
| 922 | 891 | |
| 902 | 865 | |
| 867 | 814 | |
| 830 | 792 | |
| 797 | 779 | |
| 780 | 756 | |
| 763 | 745 | |
| 746 | 732 | |
| 725 | 709 | |
| 712 | 687 | |
| 688 | 672 | |
| 672 | 642 | |
| 642 | 608 | |
| 613 | 566 | |
| 563 | 548 | |
| 540 | 515 | |
| 514 | 486 | |
| 490 | 438 | |
| 478 | 420 | |
| 440 | 395 | |
| 415 | 344 | |
| 394 | 277 | |
| 350 | 265 | |
| 298 | 247 | |
| 249 | 207 | |
| 158 | 168 | |
| 111 | 156 | |
| 85 | 111 | |
| | 84 | |

TABLE 5

FIR spectroscopy
Peak maxima

| Rivaroxaban/malonic acid cocrystal [cm$^{-1}$] | Rivaroxaban modification I [cm$^{-1}$] | Malonic acid [cm$^{-1}$] |
| --- | --- | --- |
| 490 | 484 | 453 |
| 473 | 475 | 429 |
| 458 | 458 | 244 |
| 443 | 438 | 222 |
| 439 | 418 | 176 |
| 413 | 394 | 123 |
| 400 | 350 | 86 |
| 353 | 303 | |
| 303 | 298 | |
| 292 | 283 | |
| 255 | 272 | |
| 235 | 247 | |
| 202 | 227 | |
| 169 | 209 | |
| 125 | 180 | |
| 94 | 168 | |
| | 138 | |
| | 119 | |
| | 96 | |

TABLE 6

NIR spectroscopy
Peak maxima

| Rivaroxaban/malonic acid cocrystal [cm$^{-1}$] | Rivaroxaban modification I [cm$^{-1}$] | Malonic acid [cm$^{-1}$] |
| --- | --- | --- |
| 8865 | 8837 | 8545 |
| 8479 | 8479 | 7318 |
| 7868 | 7111 | 7199 |
| 7087 | 6568 | 6989 |
| 6557 | 6445 | 5955 |
| 6440 | 6381 | 5824 |
| 6380 | 6006 | 5737 |
| 6050 | 5944 | 4687 |
| 6007 | 5889 | 4370 |
| 5896 | 5833 | 4277 |
| 5812 | 5764 | 4158 |
| 5640 | 5085 | |
| 5529 | 4911 | |
| 5216 | 4881 | |
| 5065 | 4793 | |
| 4906 | 4637 | |
| 4871 | 4483 | |
| 4815 | 4434 | |
| 4774 | 4380 | |
| 4698 | 4302 | |
| 4608 | 4232 | |
| 4412 | 4170 | |
| 4246 | 4145 | |
| 4210 | 4086 | |
| 4143 | 4031 | |
| 4096 | | |

TABLE 7

13C MAS NMR spectrometry Peak maxima

| Rivaroxaban/ malonic acid cocrystal [ppm] | Rivaroxaban modification I [ppm] | Malonic acid [ppm] |
|---|---|---|
| 30 | 36 | 37 |
| 35 | 38 | 42 |
| 38 | 43 | 91 |
| 41 | 45 | 176 |
| 44 | 48 | |
| 49 | 52 | |
| 51 | 56 | |
| 61 | 58 | |
| 62 | 64 | |
| 65 | 70 | |
| 68 | 73 | |
| 69 | 78 | |
| 74 | 120 | |
| 77 | 123 | |
| 118 | 127 | |
| 120 | 129 | |
| 121 | 131 | |
| 123 | 138 | |
| 128 | 141 | |
| 128 | 157 | |
| 137 | 162 | |
| 140 | 167 | |
| 157 | 168 | |
| 162 | 205 | |
| 169 | 207 | |
| 171 | 212 | |
| 204 | 215 | |
| 207 | 216 | |
| 213 | | |
| 221 | | |

TABLE 8

| Crystal lattice of rivaroxaban/malonic acid cocrystal | |
|---|---|
| Crystal system | triclinic |
| Space group | P1 |
| Z | 2 |
| Length of axis a [Å] | 8.8012(16) |
| Length of axis b [Å] | 9.9396(12) |
| Length of axis c [Å] | 24.981(3) |
| α [°] | 86.112(9) |
| β [°] | 87.026(11) |
| γ [°] | 76.353(10) |
| calculated density [g cm$^{-3}$] | 1.531 |

The invention claimed is:

1. A rivaroxaban/malonic acid cocrystal compound of the formula (II)

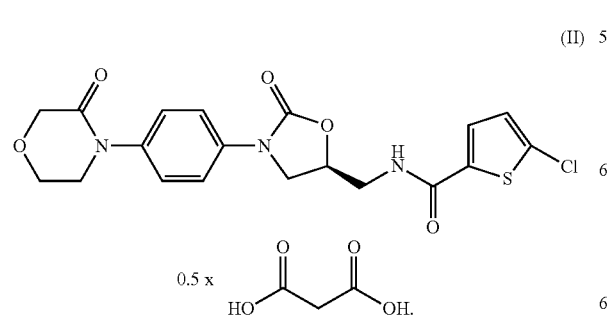

(II)

2. The compound of claim 1, characterized in that the X-ray diffractogram of the compound has a reflex at a 2-theta angle of 15.8.

3. The compound of claim 1, characterized in that the Raman spectrum of the compound has a peak at 1617 cm$^{-1}$.

4. A process for preparing the compound of claim 1, comprising dissolving rivaroxaban of the formula (I)

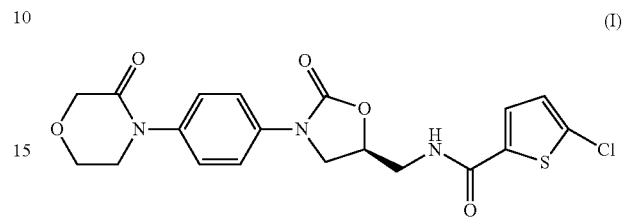

(I)

in modification I and malonic acid of the formula (III)

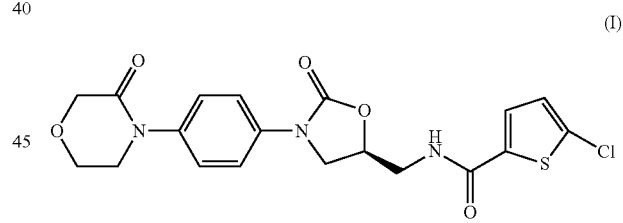

(III)

in an inert solvent at a temperature between 50° C. and 90° C. and evaporating the solvent.

5. The process of claim 4, characterized in that rivaroxaban of the formula (I) in modification I and malonic acid of the formula (III) are employed in a molar ratio of 1:1.

6. The process of claim 4, characterized in that, prior to evaporation of the solvent, the solution is seeded with crystals of the compound of the formula (II).

7. A process for preparing the compound of claim 1, comprising suspending rivaroxaban of the formula (I)

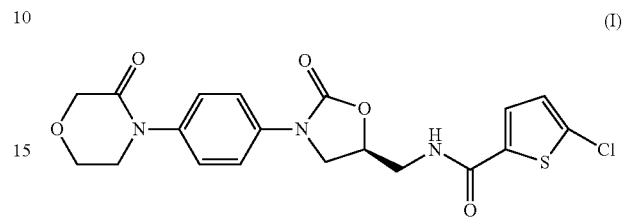

(I)

in modification I and malonic acid of the formula (III)

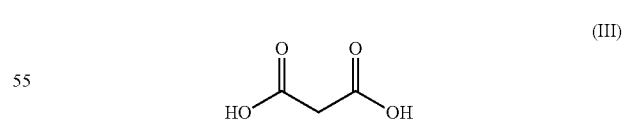

(III)

in an inert solvent at a temperature between 20° C. and 25° C. and isolating the precipitate formed.

8. A pharmaceutical formulation comprising the compound of claim 1 and an inert nontoxic pharmaceutically suitable auxiliary.

9. A method for the treatment and/or prophylaxis of thromboembolic disorders in humans and animals comprising administering a therapeutically effective amount of the compound of claim 1 to a human or animal in need thereof.

10. A method for prevention of coagulation of blood in vitro comprising adding an anticoagulant amount of the compound of claim 1 to a biological sample that contains factor Xa.

11. A method for the treatment and/or prophylaxis of thromboembolic disorders in humans and animals comprising administering a therapeutically effective amount of the pharmaceutical formulation of claim 8 to a human or animal in need thereof.

* * * * *

UNITED STATES PATENT AND TRADEMARK OFFICE
CERTIFICATE OF CORRECTION

PATENT NO. : 8,466,280 B2  Page 1 of 1
APPLICATION NO. : 12/997474
DATED : June 18, 2013
INVENTOR(S) : Grunenberg et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 263 days.

Signed and Sealed this
Eighth Day of September, 2015

Michelle K. Lee
*Director of the United States Patent and Trademark Office*